US006491618B1

(12) United States Patent
Ganz (10) Patent No.: US 6,491,618 B1
(45) Date of Patent: Dec. 10, 2002

(54) APPARATUS AND METHOD FOR DEBILITATING OR KILLING MICROORGANISMS WITHIN THE BODY

(76) Inventor: Robert A. Ganz, 1431 Lakeview Ave., Minneapolis, MN (US) 55416

( * ) Notice: Subject to any disclaimer, the term of this patent is extended or adjusted under 35 U.S.C. 154(b) by 108 days.

(21) Appl. No.: 09/598,653

(22) Filed: Jun. 22, 2000

Related U.S. Application Data (63) Continuation-in-part of application No. 09/338,687, filed on Jun. 23, 1999.

(51) Int. Cl.$^7$ .............................. A61N 5/00; A61B 17/00
(52) U.S. Cl. ............................................... 600/3; 607/88
(58) Field of Search .................. 600/169, 476, 600/477; 604/21; 606/2, 15, 7; 607/88–94

(56) References Cited

U.S. PATENT DOCUMENTS

| 2,173,258 A | | 9/1939 | Lederer |
| 3,582,702 A | | 6/1971 | Almer |
| 4,164,680 A | | 8/1979 | Villalobos |
| 4,428,744 A | | 1/1984 | Edelson |
| 4,683,889 A | | 8/1987 | Edelson |
| 4,848,336 A | * | 7/1989 | Fox et al. ...................... 606/7 |
| 4,987,007 A | | 1/1991 | Wagal et al. |
| 4,998,930 A | * | 3/1991 | Lundahl ...................... 606/15 |
| 5,041,108 A | * | 8/1991 | Fox et al. ...................... 600/7 |
| 5,059,191 A | * | 10/1991 | Beyer et al. .................. 604/20 |
| 5,090,043 A | | 2/1992 | Parker et al. |
| 5,153,900 A | | 10/1992 | Nomikos et al. |
| 5,334,171 A | | 8/1994 | Kaldany |
| 5,405,369 A | * | 4/1995 | Selman et al. ................ 607/88 |

(List continued on next page.)

FOREIGN PATENT DOCUMENTS

| EP | 0 359 724 A2 | 3/1990 |
| EP | 0 359 724 A3 | 3/1990 |
| EP | 0 572 170 A1 | 12/1993 |
| EP | 0 718 864 A1 | 6/1996 |
| EP | 0 860 180 A2 | 8/1998 |
| GB | 230 183 | 3/1925 |
| GB | 997 352 | 7/1965 |
| WO | WO 97/06549 | 2/1997 |
| WO | WO 97/07740 | 3/1997 |

OTHER PUBLICATIONS

C.E. Millson et al., Ex–Vivo Treatment of Gastric Helicobacter Infection by Photodynamic Therapy; Journal of Photochemistry and Photobiology B: Biology 32 (1996) 59–65 London.

C.E. Millson et al., The Killing of *Helicobacter pylori* by Low Power Laser Light in the Presence of a Photosensitizer; J Med Microbiology vol. 44 (1996) 245–252.

(List continued on next page.)

*Primary Examiner*—Kevin Shaver
*Assistant Examiner*—Nikita R Veniaminov
(74) *Attorney, Agent, or Firm*—James V. Harmon (57) ABSTRACT

A surgical apparatus has a body portion that includes a shaft terminating in a distal head or tip and a means for directing light radiation from the apparatus onto the lining of a body cavity for treating a gastrointestinal ailment of a patient including gastritis, gastric ulcer, duodenal ulcer, gastric cancer, gastric lymphoma, ulcerative colitis, or Crohn's disease. The method of use of the apparatus comprises inserting the shaft of the apparatus into a body cavity, e.g., stomach or colon, of the patient to place the distal tip of the shaft in the desired position. The body cavity of the patient is then irradiated with ultraviolet light radiation in a preferred range of about 250 nm to 270 nm so as to kill or debilitate microorganisms lining the body cavity without serious destruction of the body tissue of the patient to thereby improve or alleviate one or more of the symptoms of the gastrointestinal ailment. A probiotic comprising innocuous bacteria can then be administered to the patient to reestablish the growth of normal microbial flora.

26 Claims, 8 Drawing Sheets

U.S. PATENT DOCUMENTS

| | | | |
|---|---|---|---|
| 5,422,926 A | | 6/1995 | Smith et al. |
| 5,566,221 A | | 10/1996 | Smith et al. |
| 5,591,199 A | | 1/1997 | Porter et al. |
| 5,621,780 A | | 4/1997 | Smith et al. |
| 5,647,840 A | * | 7/1997 | D'Amelio et al. .......... 600/169 |
| 5,748,699 A | | 5/1998 | Smith |
| 5,855,595 A | * | 1/1999 | Fujishima et al. ............ 607/90 |
| 5,871,522 A | | 2/1999 | Sentilles |
| 6,061,591 A | * | 5/2000 | Freitag et al. .............. 600/476 |
| 6,070,096 A | * | 5/2000 | Hayashi ...................... 600/477 |

OTHER PUBLICATIONS

Martinetto P., et al. Bactericidal effects induced by laser irradiation and haematoporphyrin against gram–positive and gram–negative microorgamisms. *Drugs Exp. Clin Res.* XII (4): 335–342, 1986.

Kubey W., et al. In Vitro studies on the microbicidal effectiveness of a xenon–based ultraviolet light device for continuous ambulatory peritoneal connection. *Blood Purif.* 9 (2): 102–108, 1991.

* cited by examiner

APPARATUS AND METHOD FOR DEBILITATING OR KILLING MICROORGANISMS WITHIN THE BODY

This is a continuation-in-part of application No. 09/338,687, filed Jun. 23, 1999.

FIELD OF THE INVENTION

This invention relates to an apparatus and method for the destruction of micro-organisms on or within a body cavity of a patient through the use of ionizing radiation.

BACKGROUND OF THE INVENTION

Infections involving the human gastrointestinal tract are extremely common, involving many millions of people on an annual basis. These infections include bacteria, viruses, and fungi, and are responsible for significant illness, morbidity and, in many cases, death. While the invention has utility in destroying microorganisms in various parts of the body, e.g., the stomach, bowel, lungs, peritoneal cavity, urinary tract, etc., it is particularly useful in the treatment of gastrointestinal infections.

It has recently been shown that the most common gastrointestinal infection in the world is due to *Helicobacter pylori*, a bacterial pathogen that infects the stomach and duodenum. In the United States, for example, *Helicobacter pylori* is found in approximately 20% of the adult population. It is a chronic gut infection and, once acquired, is notoriously difficult to cure. Most infectious bacteria can be readily destroyed by the human immune system; however, *Helicobacter pylori* lives in the lumen of the stomach and on the surfaces of the stomach and duodenal cells, making it relatively resistant to a host immune response, even if vigorous. I have, however, taken advantage of its location in the treatment method and apparatus employed in the present invention.

*Helicobacter pylori* is typically a silent infection in humans, the majority of the time causing a relatively innocuous gastric inflammation or gastritis. In a significant minority of infected people, however, *Helicobacter pylori* can cause symptomatic gastritis, gastric ulcer, duodenal ulcer, gastric cancer, and gastric lymphoma. The organism is responsible for approximately 90% of all reported duodenal ulcers, 50% of gastric ulcers, 85% of gastric cancer, and virtually 100% of gastric lymphoma. Millions of Americans have symptomatic gastritis due to *Helicobacter pylori* or the much more serious entities noted above. *Helicobacter pylori* is responsible for thousands of deaths in this country due to complicated ulcer disease and cancer, and is considered to be a Class 3 carcinogen by the World Health Organization, in the same class as Benzene and DDT.

The organism is found in all countries in the world, causing the same symptoms, diseases, and deaths, but it is most prevalent in undeveloped countries, presumably due to poor hygiene, contaminated water supplies and crowding. In Peru and other South American countries, for example, the prevalence rate of *Helicobacter pylori* infection approaches 90%.

There is no vaccine available for *Helicobacter pylori* and none is anticipated in the foreseeable future, despite years of intensive effort. The only treatment currently available is prolonged and complicated antibiotic regimens involving three or four expensive antibiotics given over a two-week period. Even using a vigorous antibiotic regimen, however, up to 20% of those treated are not cured of their infection. The antibiotics used are powerful, sometimes not well tolerated, and can cause nausea, an altered taste sensation and diarrhea. Allergic reactions are not uncommon. In addition to the problems of efficacy and side effects, antibiotic resistance to this organism is growing rapidly. Up to 50% of the Helicobacter isolates are now resistant to one or more of the best antibiotics known to cure the infection. This problem of antibiotic resistance is only expected to grow in the future, leading to worsening disease outcomes and an ever-increasing health expense.

Thus, a great need exists for a new, effective, rapid and well-tolerated cure of *Helicobacter pylori*, a luminal infection of the gut. There also exists a need for a well-tolerated and effective treatment for debilitating or killing microorganisms with as little intrusion as possible in other body cavities, such as the bowel, lungs, peritoneal cavity or urinary tract.

SUMMARY OF THE INVENTION

This invention provides a treatment method and apparatus for debilitating or killing *Helicobacter pylori* or other microorganisms within the body of a patient and is especially suited for treating stomach or duodenal ulcers. The present therapeutic method involves the use of radiation for eliminating pathogenic micro-organisms within or supported upon the lining of a body cavity of a patient, e.g., the stomach. An elongated flexible shaft is provided for insertion into the body in any of various ways selected by the surgeon. It can be placed endoscopically, e.g., through the esophagus, placed surgically, placed laparoscopically or by CAT scan-guided percutaneous insertion. A radiant energy distribution head is provided at the end of the flexible shaft to provide ionizing radiation for destroying microorganisms within the body. Radiant energy, e.g., x-ray, ultraviolet light, beta radiation, gamma radiation, radio waves, microwaves, or infrared energy is then transferred from the head of the instrument to the epithelium around the head of the instrument in an amount sufficient to debilitate or kill the *Helicobacter pylori* or other microorganisms in the lining of the body cavity.

In one preferred form of instrument, the flexible shaft comprises a coaxial cable surrounded by an electrical insulation layer and has the radiant energy distribution head located at its distal end. In a preferred optional form of the invention, a positioning and distending device around the head of the instrument is of sufficient size to contact and expand the walls of the body cavity in which it is placed both in the front of the distribution head as well as on the sides of the distribution head. For example, the head of the instrument can be supported a controlled distance from the wall of the body cavity by an expandable balloon so as to regulate the amount of energy transferred to the microorganisms. The balloon is preferably bonded to a portion of the flexible shaft at a point spaced from the head. The radiation can be x-ray energy, infrared, ultraviolet, radio waves, microwave, beta radiation or gamma radiation. Other forms of radiant energy that can be used for killing or debilitating surface microorganisms will be apparent to those skilled in the art.

These and other more detailed and specific objects of the present invention will be better understood by reference to the following figures and detailed description which illustrate by way of example of but a few of the various forms of the invention within the scope of the appended claims.

DETAILED DESCRIPTION OF THE INVENTION

The therapeutic method in accordance with the present invention is suited for use in various body cavities including, but not limited to, the stomach, the bowel, the lungs, the peritoneal cavity, the urinary tract, and can also be used with various devices, fabrication methods, arrangements, systems and methods of employment which irradiate the walls of various body cavities or interior sites within the body of a patient by means of radiation in sufficient amount to debilitate or kill microorganisms lining the body cavity in which the invention is used In one preferred form of the invention, an x-ray device is provided which includes components for producing localized x-ray radiation within a vacuum housing or tube and, optionally, including an inflatable balloon surrounding the vacuum housing and preferably connected near the distal end of the device for positioning the source of radiation as well as for expanding the walls of the body cavity. While the invention can be employed for killing or debilitating various pathogenic microorganisms, it can be used to advantage in treating *Helicobacter pylori* infections of the gastrointestinal system and other ailments in which ionizing radiation is to be delivered to portions of the body that are not easily accessible. In order to provide a better understanding, the present invention will be described by way of example in the treatment of *Helicobacter pylori* infections within the stomach. It should be understood, however, that the invention is not limited to specific apparatus or methods described.

*Helicobacter pylori* is an infection of the stomach and duodenum and the major cause of stomach ulcers. Various forms of radiation, including x-rays, radiation from isotopes, radio waves, microwaves, or light radiation, e.g., ultraviolet light in accordance with the invention provide an advantageous method of treating such infections. The x-ray device, for example, produces ionizing radiation that penetrates the lining of the body cavity, in this case the columnar epithelial lining of the walls of the stomach, or the epithelium of any other passage or lumen that is being treated. During this treatment, the radiation produces apoptosis or programmed cell death in which the DNA of the microorganism is rendered unable to divide. The apoptosis that occurs in the microorganisms is different from necrosis, another type of cell death. In apoptosis produced by the radiation, a disruption of the gene structure of the microorganism prevents it from further replication. Consequently, the microorganisms die by mutation and, in some cases, by the disruption of metabolic processes at the cellular level. Some fraction of the microorganisms may also be killed immediately by the radiation. An important advantage of the invention lies in the fact that many organisms, such as bacteria, are exquisitely sensitive to radiation, sensitive to a much greater degree than the surrounding human cells. Accordingly, the bacteria can be killed or debilitated by apoptosis without serious destruction of the host cells.

In one aspect of the present invention, a source of ionizing radiation such as an x-ray device is positioned in a body cavity, e.g., the stomach, for treating *H. pylori* infections by inducing apoptosis in the bacterial cells carried on or within in the epithelium lining the stomach. The x-ray or other ionizing radiation of the present invention can therefore be used to prevent the escalation of the infection to stomach ulcers and cancer.

Refer now to the figures wherein the same numbers refer to corresponding parts in the several views. FIGS. 1–4 illustrate by way of example one method of use in accordance with the present invention; the treatment of *Helicobacter pylori* infections of the stomach designated by the numeral 5. Numeral 5a indicates the esophagus and numeral 5b indicates the pyloric sphincter. In this case, an instrument 6 is provided which includes a flexible supporting cable or shaft 7 and a distal ionizing radiation distribution head 8 from which radiation emanates as shown by rays 9 that strike the adjacent lining of the stomach where the *H. pylori* infection thrives in the epithelium and mucous lining the stomach 5. In this case, the source of ionizing radiation is an x-ray device 10 that includes a cathode 16, an anode 18, and a getter 24, all disposed within a vacuum chamber or tube wall 28 (see especially FIGS. 3 and 4). The cable or shaft 7 permits a physician to maneuver the x-ray device 10 to the treatment site in the body. It is contemplated that different types of maneuvering devices could be employed to position the head 8 containing the x-ray device 10 which provides the ionizing radiation, depending upon the particular site to be treated. In the embodiments showing the use of the instrument 6 in the stomach and gastrointestinal system, it is helpful for the shaft 7 to be flexible, to have a reduced diameter and rounded forward end such that it can be easily introduced into the esophagus and stomach, either by itself or, if desired, through an appropriate flexible endoscope (not shown). In one particular embodiment, the shaft 7 will have an outer diameter of less than or equal to approximately 3 mm, allowing it to fit easily within a standard endoscope that typically has a working lumen diameter of about 3 mm. In other applications, the properties and dimensions of the shaft 7 may vary to meet the requirements of the task.

For many disorders, an annular or donut-shaped radiation pattern 9 is ideally suited for treatment. In order to achieve this pattern, many passages and other interior portions of the body need to be dilated while treatment is carried out with ionizing radiation from the x-ray device 10. The stomach is very soft and, except after a meal, is in a collapsed state. Rugae or folds 5c are present on its inner walls. Stomach ulcers resulting from an H. pylori infection are shown at 5d. In one preferred embodiment of the present invention an optional dilating balloon 20 can be provided, if desired, to dilate the passage of the body, such as the stomach, and thereby distend the stomach wall and hence spread the rugae 5c apart and thus. flatten the stomach wall so that a uniform annular radiation pattern can be created. The balloon 20 can also be important in positioning and holding the distribution head 8 in the desired location, especially in a central position that is equidistant from all parts of the surrounding stomach wall so as to provide the same dose of radiation to all portions of the stomach 5 surrounding the distribution head 8.

When using a small x-ray emitter, a problem is sometimes encountered when too much heat is produced at the anode during operation. If water circulates through the balloon interior, it further serves to cool the x-ray emitter and dissipate the potentially damaging heat. If desired, the balloon 20 can be in fluid communication with a fluid loop 22 that is disposed within the shaft 7 to carry fluid from outside the body to the interior of the balloon 20, and provide a return path for the fluid. If desired, the fluid in loop 22 can circulate in the interior of the balloon 20, inflating the balloon 20, and can then be returned to the proximal portion of the shaft 7 through the fluid loop 22. A circulating pump 34 can be used to circulate the fluid and maintain the pressure required to achieve the desired balloon size. The pump 34 can be coupled to the fluid loop 22 via fluid ports 35. Other methods and devices known in the art may also be used to circulate the fluid and inflate the balloon 20.

Figure 3:
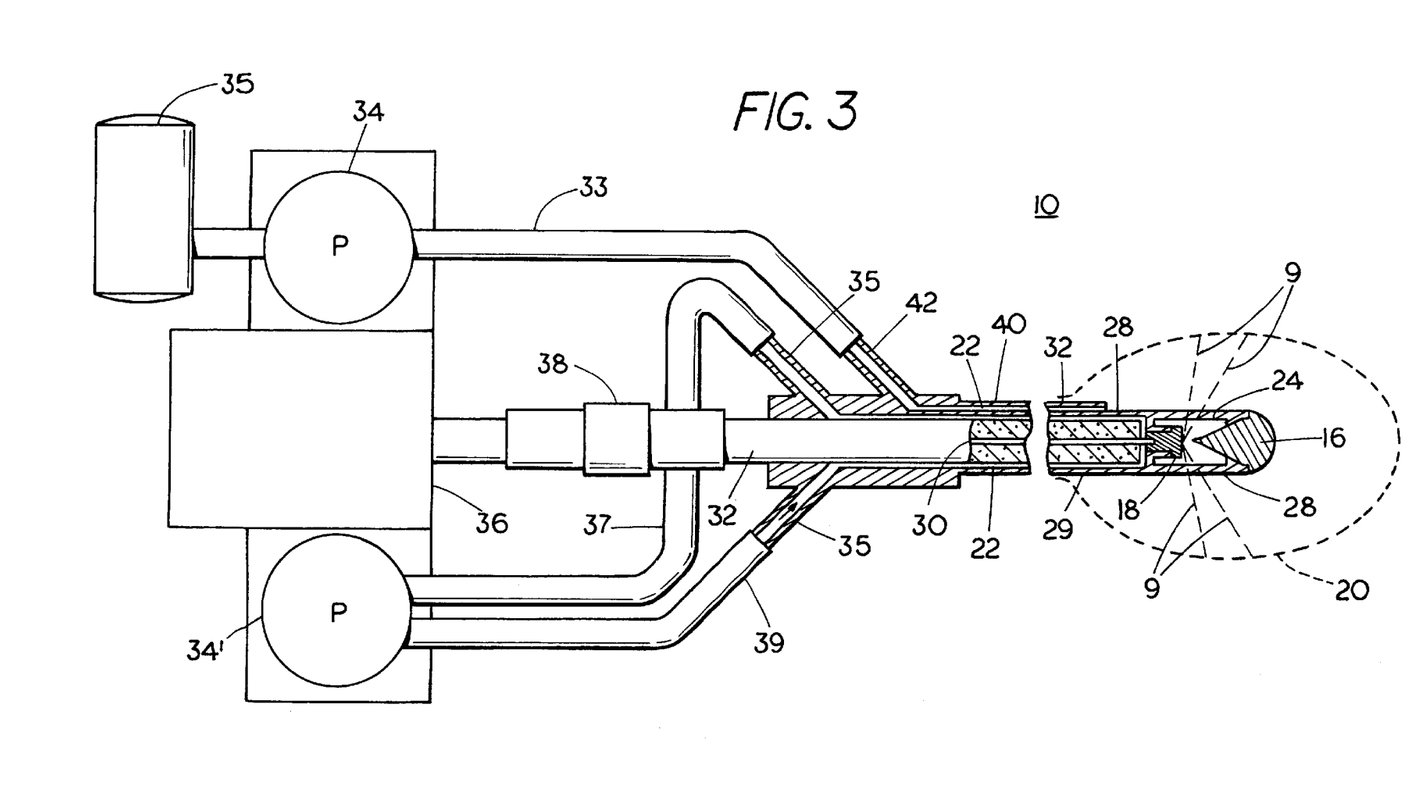
FIG. 3 is a diagrammatic, longitudinal, cross-sectional view of an instrument and supporting equipment in accordance with one form of the invention.
Figure 4:
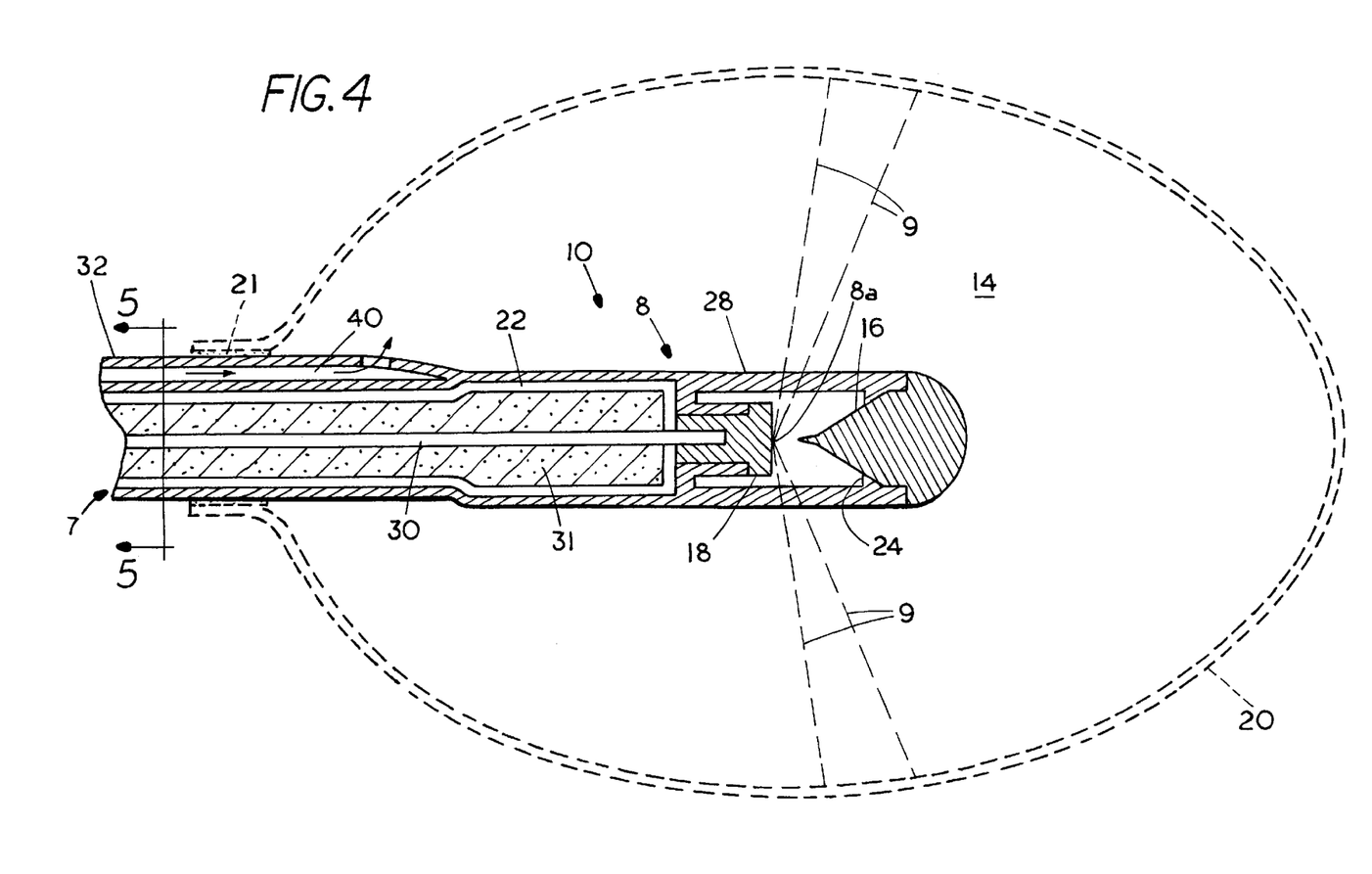
FIG. 4 is an enlarged longitudinal cross-sectional view of the distal end of an instrument in accordance with one form of the invention.

Since it is generally desirable to provide independent control of the balloon size and cooling rate, a separate inflation lumen 40 and port 42 are shown in FIGS. 3 and 4 in fluid communication with the balloon 20. The fluid loop 22 is positioned to circulate cooling fluid in heat conducting relationship with the anode 18. In the embodiment shown in FIG. 3, the fluid loop 22 extends to surround a portion of the anode 18. The circulating action of the fluid loop 22 can thus provide a constant cooling rate, regardless of the extent of balloon dilation. The separate inflation lumen 40 can be coupled to a fluid source of adjustable pressure for the balloon 20 via the inflation port 42. In one embodiment, the fluid loop 22 and the inflation lumen 40 are created using plastic extrusion techniques. This arrangement has the advantage of allowing a liquid, e.g., water, to be used in fluid loop 22 for cooling and a gas, e.g., air, to be used for balloon inflation via lumen 40 so that the radiation from head 8 is not absorbed before reaching the stomach wall. Different cooling mechanisms could also be used.

Thus, during use, an inflation fluid is provided to expand the balloon 20 via lumen 40, inflation port 42 and a line 33 which is connected to the pump 34. If a liquid is used instead of a gas such as air, the liquid, e.g., water or saline, can be supplied from tank 35 which is connected to the inlet of pump 34. A gas is, however, preferred for filling the balloon 20, since it will have a negligible tendency to attenuate the radiation 9 emitted from the energy supply head 8. The coolant is circulated separately through the fluid loop 22 via lines 37 and 39 by means of circulating pump 34'. The pumps 34 and 34' are controlled by the power supply 36 which also supplies the high voltage current through the coaxial cable via coupling 38 to a cathode 16 and an anode 18 that are contained within a vacuum tube or chamber 28. The power supply 36 also includes an x-ray detector of suitable known construction that is used to calibrate the output of the device and control dosimetry, as well as an electronic display, if desired, for monitoring the therapy.

In order to apply an electrical field across the anode 18 and cathode 16, the anode 18 and cathode 16 are coupled to the power supply or high voltage source 36. In this embodiment, a coaxial cable is disposed within the flexible shaft 7 and coupled to the high voltage source 36 at the proximal end of the shaft 7. An internal conductor 30 of the coaxial cable is coupled to the anode 18 at the appropriate voltage and is enclosed in an insulating layer 31. An external conductive layer 32 of the coaxial cable is held at ground and coupled to cathode 16. A conductive solder on the outside of the vacuum chamber wall 28 may be used to couple the cathode 16 to the external conductive layer 32. Other known methods may also be used to apply an electric potential across the anode and cathode.

The vacuum tube 28 containing the cathode 16 and anode 18 can be of the thermonic type, with x-ray energies of, say, 8 KeV to 20 KeV. The tube can be powered to utilize 3 watts or less to produce soft x-ray radiation. A typical treatment time at 3 watts is about one to 20 minutes. When the prescribed dose of ionizing radiation has been delivered, the x-ray tube is turned off and the x-ray distribution head 8 is removed. When a radioactive isotope source is used instead of an x-ray source, the tissue is exposed to ionizing radiation for a few minutes, usually from about 15 minutes to 30 minutes.

The stomach in its relaxed state has a diameter of about 5–6 centimeters and cannot accommodate a rigid structure. In one embodiment, the device of the present invention can be inserted by being passed through a standard flexible laryngoscope or endoscope (not shown) that has a working lumen about 3 millimeters in diameter. Therefore, a coaxial cable used in this device must have a diameter small enough to be accommodated within the passage to be treated or within the scope-device used, and it must be able to carry the required voltages and have sufficient flexibility to make turns as it follows the passage. A diameter of less than or equal to 3 millimeters may be used for most applications. Standard high voltage coaxial cables are generally not flexible enough. Miniature high frequency coaxial cables are available with an outer diameter of approximately 1.0 mm to 3.0 mm which also exhibit sufficient flexibility and can carry the required voltage without breakdown. In one embodiment of the invention, a cable with an outer diameter of less than or equal to about 3 mm is used. Cables approximately 1–2 mm in diameter are also available, and are used in other embodiments. Such cables are manufactured by, for example, New England Electric Wire Corporation, Lisborn, N. H.

In one embodiment, a getter 24 is disposed within the vacuum housing 28 in order to aid in creating and maintaining a vacuum condition of high quality. The getter 24 has an activation temperature at which it will react with stray gas molecules in the vacuum. After the vacuum housing is assembled under vacuum conditions and the housing pumped out or baked out, the device is heated to the activation temperature and maintained at that temperature for several hours. It is desirable that the getter used have an activation temperature that is not so high that the x-ray device will be damaged with heated to the activation temperature. An SAES ST 101 alloy getter may be used, which has an activation temperature in the range of 750° C. to 900° C. and is composed of approximately 64% zirconium and 16% aluminum. An ST 707 alloy getter also may be used, which has an activation temperature in the range of 300° C. to 500° C. and is composed of approximately 70% zirconium, 18.6% vanadium, and 5.4% iron. Other suitable getters such as alkali metals can be used, if desired.

Figure 1:
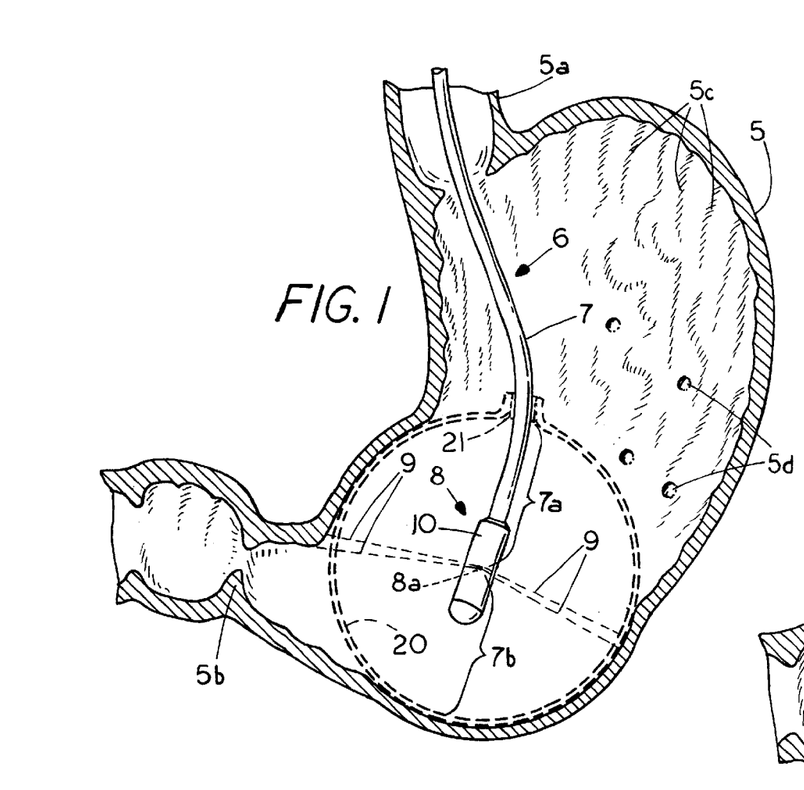
FIG. 1 is a vertical cross-sectional view showing the use of the invention in the stomach.
Figure 2:
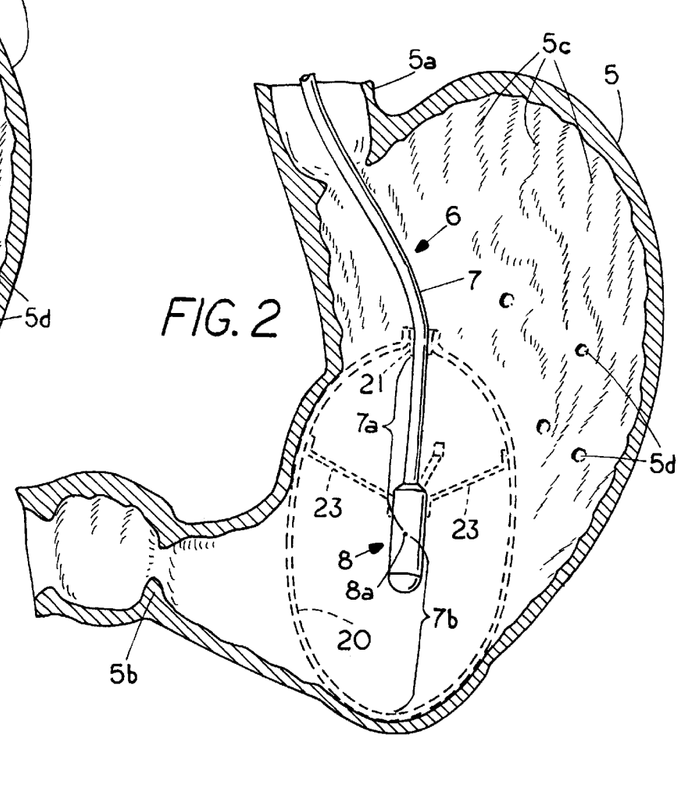
FIG. 2 is a view similar to FIG. 1 showing an elliptical balloon in use for positioning an ionizing radiation source in the stomach.

In order to most effectively decelerate the electrons striking the anode, a heavy metal material such as tungsten or gold can be used for the anode 18. The cathode and anode will be shaped to produce the desired radiation pattern. In the embodiment of FIGS. 1 and 2, the anode 18 is cylindrically shaped with a flat, circular side disposed toward the cathode 16, and the edge is rounded. The cathode 16 of this embodiment is cone-shaped.

A wall of the vacuum chamber 28 should be transparent to x-rays in order to allow the full dosage to reach the wall of the body cavity being treated. The wall 28 can comprise pyrolytic boron nitride, or another metal or ceramic material which is transparent to x-rays. Other possibilities include beryllium, beryllium oxide, aluminum, aluminum oxide, or graphite. In one embodiment, the outer diameter of the x-ray device is sized as large as, say, 1 centimeter to deliver the localized radiation to the interior of the stomach. In another embodiment, the outer diameter of the x-ray device is less than or equal to about three millimeters.

In some applications, such as use in the stomach, the diameter of the dilated balloon 20 should be able to vary with the pressure applied, so that the diameter of the balloon can be adjusted to fit the size of the patient's stomach or other passage. Therefore, an elastic balloon is particularly suited to gastric applications, where the elastic material will conform to the many surface features of the stomach and dilate the stomach more completely. However, in other applications, it may be desirable to employ an inelastic balloon with a fixed dilated diameter. It should be noted in FIG. 1 that the balloon 20, when present, is preferably secured to the flexible shaft 7, e.g., by means of a suitable adhesive 21 at a distance 7a from source 8a and also spaced from the radiation head 8. The distal end of the balloon 20 is free rather than being connected to the distribution head 8 or to anything else and is spaced from the source 8a of radiation by a distance 7b that is equal to 7a. The distances 7a and 7b each equals the approximate radius of the balloon 20 so as to locate the source 8a of the radiation 9 at the center of balloon 20, thus equalizing radiation flux in all directions. A round balloon is shown in FIG. 1.

In the x-ray device, an electric field exists at the cathode 16, while on the outside of the vacuum housing a conductive braid or solder is held at ground. These two potentials can be insulated from each other to reduce the chance of electrical shover. A vacuum tube wall of pyrolytic boron nitride can provide some insulation. If a metal is used as the wall of the vacuum chamber 28, an insulating layer is beneficial to decrease the chance of electrical flashover. As additional protection against electrical flashover, an electrically insulating material can be placed at the joints on the outside of the vacuum chamber wall 28. The insulating material could be a potting compound, an injection-molded polymer, and other materials with electrically insulating properties. The vacuum chamber further includes a biocompatible outer coating, such as polyethylene or Teflon® material. The joints between the vacuum chamber wall 28 and the anode 18 may be vacuum furnace brazed, or may be sealed by conventional crimping methods.

The cathode 16 of the present invention consists of a material which displays emission characteristics when an electrical field is applied. One possible cathode material is a thin diamond film, which can be formed using conventional chemical vapor deposition techniques. A diamond film also may be formed using a laser ion source as described in U.S. Pat. No. 4,987,007 to Wagal, the contents of which are incorporated herein by reference. A graphite target and the substrate to be coated are disposed in a vacuum chamber. Between the two is an accelerating grid held at a high negative potential. The graphite target is radiated with a focused laser beam from a pulse laser. The laser beam ejects a plume of carbon vapor from the graphite target. A portion of the atoms in the plume are ionized by the focused laser beam, and the positive carbon ions are accelerated towards the substrate by the accelerating grid.

One possible cathode material is described in U.S. Pat. No. 6,377,846, the contents of which are incorporated herein by reference. The cathode material is a coating of carbon having diamond-like bonds which demonstrate negative electron affinity. It is also desirable to have sufficient conductivity to create a constant supply of electrons to the surface of the cathode. The presence of some graphite bonds in the diamond film will contribute to conductivity. Thus, a combination of a diamond film having both sp3 carbon bonds, to function as a cathode, and some sp2 carbon bonds, to facilitate conductivity, is particularly suited for use in many applications. Other elements may also be present in the film in small quantities. The diamond film will have the property that it can emit electrons at electrical fields greater than or equal to about 20 KV/micron. This required electric field is significantly lower when compared to that required for metal emitters such a molybdenum or silicon, which require greater than 1,000 KV/micron. If desired, the x-ray device can be constructed as described in U.S. Pat. No. 6,095,966 and is incorporated herein by reference.

When used to radiate the walls of an interior passage of the body, according to one embodiment of the invention, the x-ray device may be placed within a standard endoscope or laryngoscope. The x-ray device or other ionizing radiation described herein is introduced into the passage to be treated. The x-ray device, etc., is then guided through the passage, using techniques known in the art, until it is positioned near the area to be irradiated. The site to be irradiated may be viewed through the endoscope, and the area around the device may be flushed using the endoscope, if necessary. The dilating balloon 20 is then inflated by fluid, either liquid or gas, from the fluid pump to the desired diameter to expand the body cavity, in this case the stomach so as to hold the radiation distribution head 8 in the desired location and spread the rugae 5c apart so as to thereby flatten the stomach wall to insure uniform irradiation.

During operation, the high voltage generator is activated and an electrical field is established across the cathode 16 and the anode 18. The cathode 16 emits electrons which are accelerated toward the anode 18. As the electrons are decelerated by the anode 18, electromagnetic ionizing radiation is emitted. In this manner, x-ray radiation is produced by the Bremsstrahlung effect. As the x-ray radiation impinges upon the wall of the body cavity, such as the stomach, the *H. pylori* living on the surface of the passage are killed or debilitated by apoptosis as discussed above. In *H. pylori* infections, for example, the apoptosis eliminates the bacterial cells and reduces inflammation as well as the biochemical results of inflammation, thereby preventing ulcers, gastritis and cancer. When the desired dosage has been delivered, the voltage source is turned off and the balloon 20, when present, is deflated. The device is then withdrawn from the body.

The dosage of x-ray radiation to be applied to the interior of a body will generally be within the scope of the attending physician's judgment and will be based on individual conditions, such as the severity of the infection and the damage that has occurred at the site to be treated and the particular patient. In order to treat *H. pylori*, only the surface of the epithelium needs to be irradiated.

According to the present invention, x-ray radiation typically in the range of 0.1 to 50 Grays, and most preferably 1–2 Grays, may be applied. The treatment is typically structured to last about 2 to 10 minutes, and most preferably, 3 to 5 minutes. The x-ray emitter may be repositioned by moving it from one part of the stomach to another, either continuously or intermittently during the course of radiation treatment, depending on the length of the area requiring treatment.

It will be noted that because the source of radiation in the distribution head 8 is at the center of the balloon 20, all of the rays 9 will be of the same length when they strike the microorganisms, thereby assuring uniform radiation flux and, consequently, uniform exposure to radiation wherever the radiation strikes the wall of the cavity that is being treated. Uniform radiation exposure is also aided through the flattening of the stomach wall that is accomplished by the expansion of the balloon 20. The expanded balloon 20 also locks or wedges the radiation-supplying head 8 in place within the stomach 5, so that stomach contractions, which take place normally, cannot displace the instrument 6. During use, the balloon 20 should not be expanded to the point where the blood supply to the epithelium lining the stomach is cut off, since oxygen is necessary in forming free radicals which are important in the destruction of the microorganisms.

Refer now to FIG. 2 which illustrates a positioning balloon 20 of a different shape. In this case, the balloon 20 is generally elliptical in shape and is secured as already described in FIG. 1 by means of adhesive 21 at a distance 7a from the energy-supplying head 8, the space 7a being a substantial distance that is determined so as to place the energy distribution head 8 in approximately the center of the elliptically-shaped balloon 20. The axis of the ellipse is aligned with the distribution head 8. If desired, in order to prevent the head 8 from dangling away from the center of the balloon 20, optional radially extending tethers 23 that serve as positioning ligaments can be bonded at each end to extend between the distribution head 8 and the wall of the balloon 20. The tethers 23 can be formed from short lengths of cord, tape or narrow strips of cloth, etc. Other positioning means for locating the head 8 at the center of the balloon 20 will be apparent to those skilled in the art. The tethers 23 can be attached to the balloon 20 by adhesive during assembly while the balloon is everted, i.e., inside out over the distal end of the distribution head 8.

Figures 5, 6, 7:
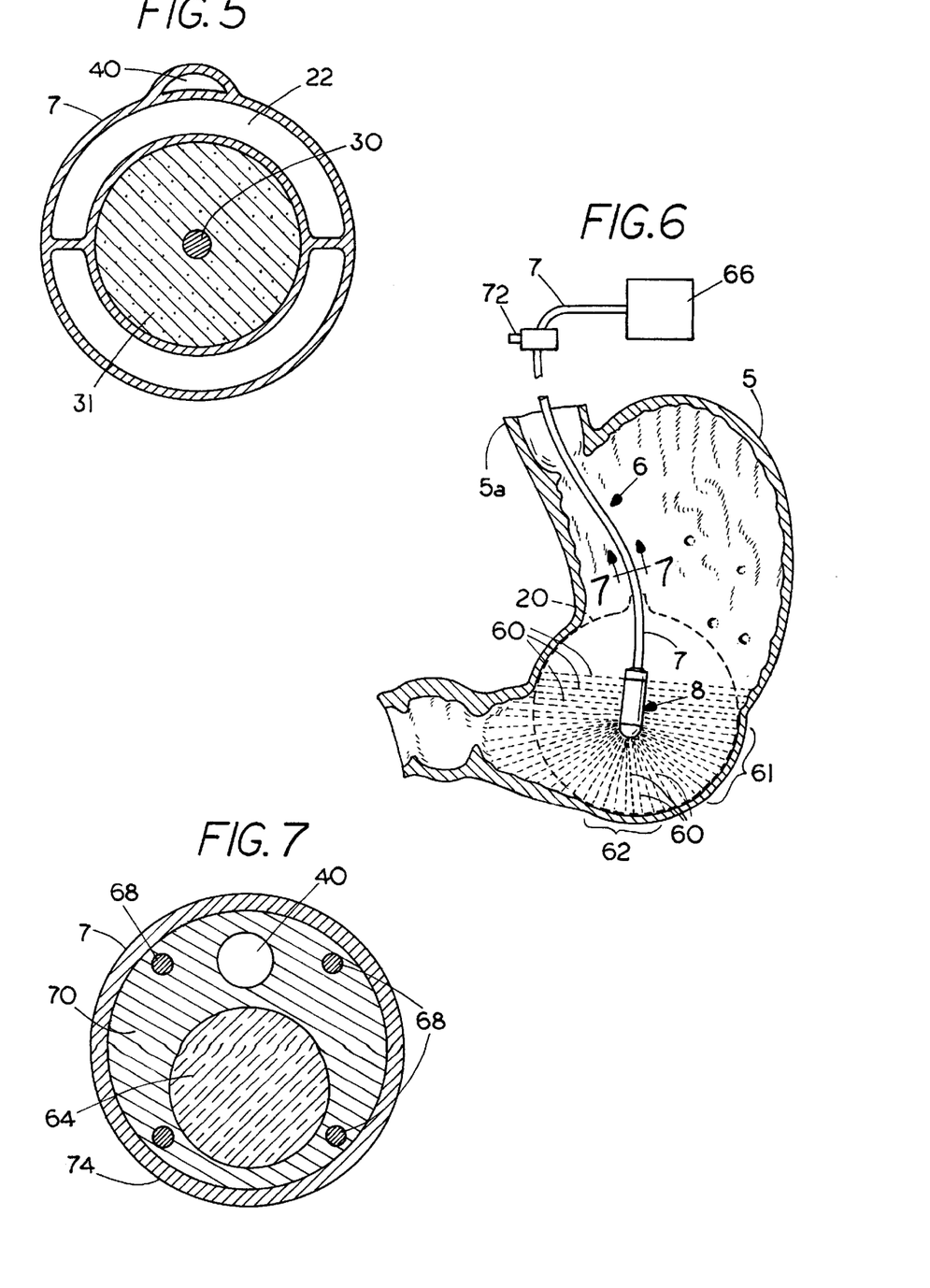
FIG. 5 is a vertical cross-sectional view taken on line 5—5 of FIG. 4.
FIG. 6 is a vertical cross-sectional view of another form of the invention shown as it appears during use in the stomach.
FIG. 7 is a transverse cross-sectional view taken on line 7—7 of FIG. 6 but on a larger scale.

Refer now to FIGS. 6 and 7 illustrating a modified form of the invention in which the same numerals refer to corresponding parts already described. In this case, ultraviolet light rays 60 are provided by the energy distribution head 8 which is formed from a transparent material, e.g., glass or fused quartz. The ultraviolet light 60 is projected both laterally at 61 as well as passing forwardly at 62 through the balloon 20 striking the wall of the stomach 5.

The balloon 20 holds the radiant energy distribution head 8 in the desired position and also distends the wall of the stomach 5 so as to spread out the rugae 5c and thereby allow uniform exposure of the portion of the wall of the stomach that is being treated. As the ultraviolet light rays 60 strike the columnar epithelium lining the stomach, the *H. pylori* infecting the cells is killed or debilitated. The part of the stomach exposed to the ultraviolet light rays 60 can be changed by the physician, either by moving the balloon 20 and head 8 along the length of the stomach 5 toward the esophagus 5a or by changing the angle of the head 8 with respect to the longitudinal axis of the stomach 5 as will be described more fully below. The position of the instrument can also be confirmed using fluoroscopy or a CAT scan, if desired.

In this case, the cathode 16 and anode 18, as well as the conductor 30, are eliminated and replaced by a fiber optic bundle 64 (FIG. 7) which extends from a light source 66 (FIG. 6) through the entire length of the flexible shaft 7 via the esophagus 5a into the stomach 5, so as to carry ultraviolet light from the source 66 through the distribution head 8 to a light reflector or diffuser, e.g., of conical shape, inside the distribution head 8 which spreads the ultraviolet light rays 60 so that they pass through the balloon 20, striking the wall of the stomach 5 to the side and in front of the distribution head 8. As shown in FIG. 7, the inflation fluid for the balloon 20 is supplied through a lumen 40 as already described. The flexible shaft 7 can be provided with a plurality of longitudinally extending, radially spaced apart cables 68 that are slidably mounted in the flexible body portion 70 of the shaft 7. Using a suitable commercially available steering mechanism for shortening or lengthening the cables 68, the distribution head 8 can be made to point toward the right, left or up and down as directed by the physician to distribute the beam of ultraviolet light to various parts of the stomach as desired. The shaft 7 can be enclosed in a protective cover or sheath 74, e.g., polypropylene plastic that will slide easily through the esophagus 5a.

The ultraviolet light source 66 can comprise any suitable commercially available lighting source, e.g., a mercury vapor lamp. There are three classes of ultraviolet light: UVA (320 nanometers to 400 nanometers), UVB (290 nanometers to 320 nanometers), and UVC (200 nanometers to 290 nanometers). UVA can be provided from an incandescent source such as a tungsten, halogen or quartz iodide lamp. UVB can be provided by means of a suitable arc lamp such as a high pressure mercury lamp or a hot quartz lamp. UVC can be provided from an arc lamp using mercury vapor, a cold quartz lamp or a carbon arc lamp which mimics sunlight with a spectrum of from 280 nanometers to near infra-red. While any suitable ultraviolet light beam can be provided, it is preferred to use UVB or UVC light because of their greater effectiveness in killing or debilitating microorganisms through apoptosis.

To use the apparatus of FIGS. 6 and 7, the shaft 7 and head 8 are passed through the esophagus 5a conventionally with the balloon 20 in a collapsed position surrounding the head 8. After the head 8 is properly positioned in the stomach 5 under the control of the physician, the balloon 20 is inflated by passing a suitable fluid, e.g., air, through the inflation lumen 40 until the balloon 20 has expanded the stomach 5 at the desired location, thereby distending the rugae so that the pockets otherwise present are spread out evenly over the surface of the balloon 20. The light source 66 is then turned on, causing the UV light to pass through the fiber optic bundle 64 and out through the distribution head 8. The distribution head 8 and the balloon 20 can then be repositioned in the stomach as desired to expose all of the infected areas or, alternatively, the control cables 68 can be manipulated so as to point the head 8 toward the areas of the stomach that require treatment. Observations can be carried out by means of a viewing port and eyepiece 72 of known construction or through a separate endoscope (not shown) that is passed through the esophagus 5a into the stomach 5 alongside the flexible shaft 7.

In another form of the invention, the same apparatus is employed as already described in FIGS. 6 and 7, except that the light source 66 comprises a suitable commercially available infrared light source. In this case the light source 66 can, for example, be an erbium laser, which is preferably operated intermittently and on low power compared to the power used for removing skin blemishes, scars, tattoos, etc., to enable the microorganisms to be killed without damaging the surrounding tissue.

Figure 8:
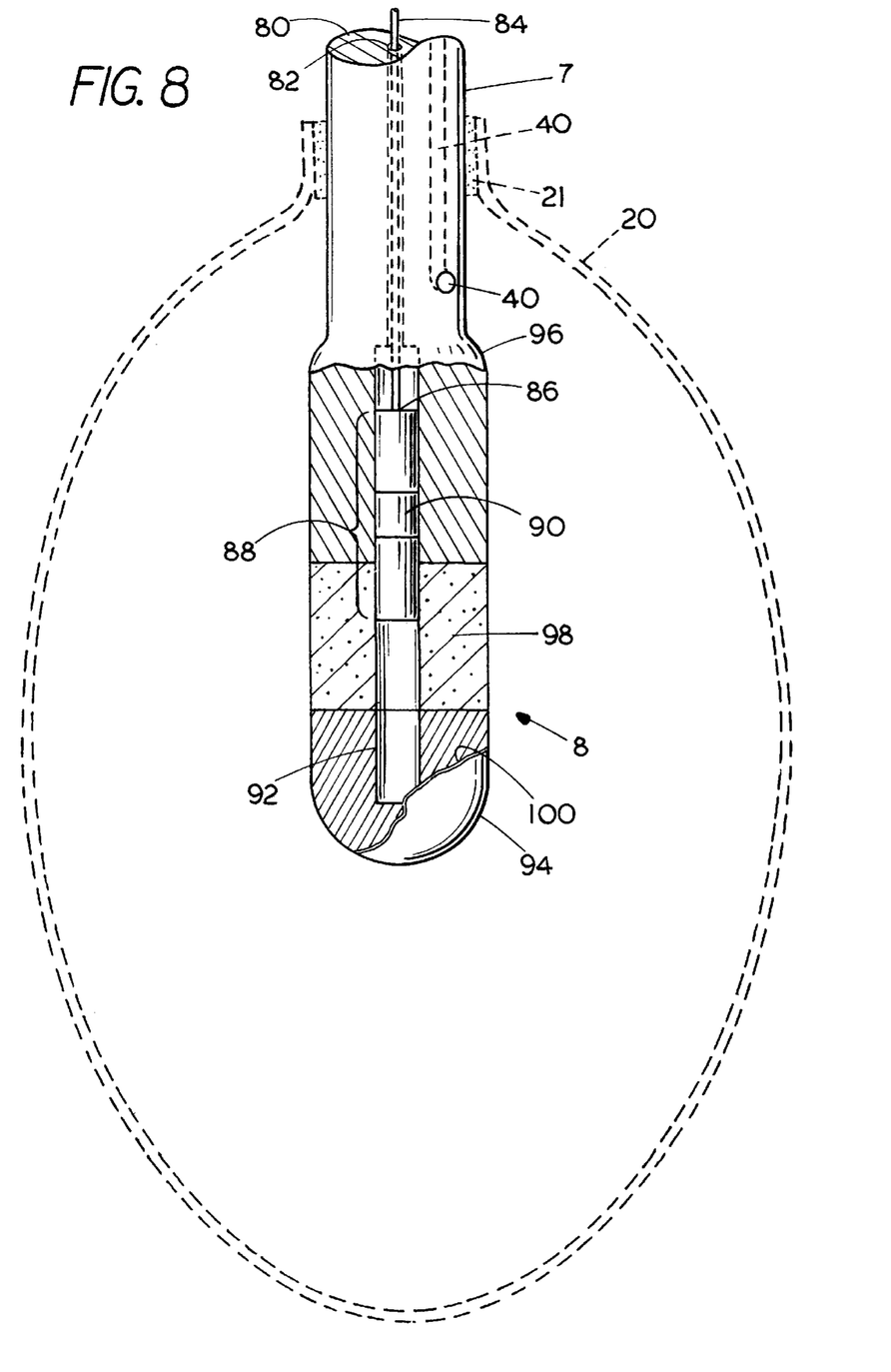
FIG. 8 is a cross-sectional view of the invention in use with a radioactive isotope employed for providing ionizing radiation.

Refer now to FIG. 8 which illustrates the use of the invention with radioactive isotopes to provide ionizing radiation for killing or debilitating *H. pylori* or other microorganisms through apoptosis. Radioactive isotopes provide the ionizing electromagnetic radiation through radioactive decay that can expose healthcare workers to radiation and require a shielded room. The present invention provides a way of shielding the isotope before and after use. In this case the flexible shaft 7 has a body portion 80 that is uniform throughout and contains a longitudinally extending lumen 82 in which a control cable 84 is slidably mounted. The distal end 86 of the control cable 84 is secured to a cylindrical slug 88 that is formed mostly of a shielding material such as lead but has a central portion 90 which is formed from a radioactive isotope. The slug 88 is slidably mounted in a bore 92 within the energy supply head 8 which includes two shielding portions including a distal portion 94 and a proximal portion 96, both formed of a suitable shielding material such as lead that is useful in shielding radioactive material. The shields 94, 96 are joined by an annular central portion 98 formed from a radiation-transparent material such as a suitable ceramic or plastic resinous material which allows radiation to be emitted when the slug 88 is moved under the direction of the physician distally so that the radioactive isotope 90 is exposed in the radiation transparent area 98 at the center of the distribution head 8. The distribution head 8 is enclosed in a sheath or coating of biocompatible material 100 such as polyethylene or Teflon®.

During use with the cable 84 pulled up, the shaft 7 and head 8 are inserted through the esophagus 5a into the stomach 5 conventionally, with the balloon 20 in a collapsed condition. Inflation fluid is then forced through the inflation lumen 40 into the balloon 20 to expand it sufficiently to spread out the walls of the stomach as described above. The cable 84 is then moved distally so as to shift the slug 88 containing the radioactive isotope 90 downwardly in FIG. 8 until the radioactive material 90 is aligned with the annular radiation-transparent wall 98, thereby allowing the ionizing radiation to pass from the radioactive isotope 90 radially in all directions from the head 8. After passing through the balloon 20, the radiation will strike the wall of the stomach 5 or other body cavity, killing or debilitating the *H. pylori* or other pathogenic microorganisms lining the wall of the cavity being treated. As treatment progresses, the balloon 20 and/or head 8 are repositioned under the control of the physician so as to redirect the ionizing radiation to the desired areas and for the length of time required to accomplish the required treatment. Because bacteria are much more sensitive to ionizing radiation than human tissue, the *H. pylori* and other bacteria can be killed or debilitated by apoptosis with little, if any, damage to the host tissue. As soon as the treatment is completed, the cable 84 is pulled, causing the slug 88 to slide proximally in the head 8 until the isotope 90 is completely surrounded by the lead shielding. The balloon 20 is then deflated and the instrument is withdrawn. As described above, the instrument shown in FIG. 8 can be positioned in any suitable manner, e.g. by observation through an endoscope (not shown) that is inserted through the esophagus alongside the shaft 7 into the stomach 5.

Any of the instruments 6 (including the shaft 7, head 8 and balloon 20) of FIGS. 1–8 can be inserted into the body cavity alone or, if desired, through the lumen of a commercially available endoscope of suitable known construction.

Isotopes emit ionizing radiation through the phenomenon of nuclear disintegration The ionizing radiation supplied by the isotope 90 can be either beta or gamma radiation. The beta radiation does not have the penetrating power of the gamma radiation, which will pass entirely through the body and into the room surrounding the patient, therefore requiring a radiation-shielded operating room. It is preferred that the ionizing radiation used have relatively shallow penetrating power, since there is usually no reason to go to any substantial depth. *H. pylori*, for example, is located on the surface of the epithelium lining the stomach. It is contemplated in accordance with the present invention to select the penetration depth of the ionizing radiation so that it penetrates only into the surface layer where the *H. pylori* is located, thereby protecting the patient from unnecessary radiation damage. For that reason, when an isotope is used to supply ionizing radiation, beta radiation is preferred to gamma radiation because of its reduced penetrating power.

In general, the use of non-radioactive sources is preferred to the radioactive source described in connection with FIG. 8, since the use of radioactive sources requires special handling, environmental considerations, and is subject to greater radiation danger. In the United States, only radiation oncologists can prescribe a therapy and dose involving radioactive isotopes. Moreover, gamma sources require a shielded catheterization laboratory. Because of the penetrating power of gamma radiation, the healthcare workers must leave the room while the patient is being treated. When gamma radiation is employed, the isotope 90 can comprise radioactive iridium-192 ($Ir^{192}$) which is available in the hospital because of its use in cancer treatment. Alternatively, a suitable beta radiation source such as potassium-32 or strontium-90 can be used as the isotope 90. Beta sources typically have a soft tissue penetration depth of less than 1.25 cm. and therefore reduce the unwanted exposure of healthy tissue compared to gamma radiation. Beta sources are also easier to handle than gamma sources and pose a smaller risk to the patient and healthcare worker.

Radio waves and microwaves can also be used in accordance with the invention for destroying pathogenic microorganisms such a *H. pylori* in the lining of a body cavity. Microwave energy can be supplied to the distribution head 8 of the device shown in FIGS. 6 and 7 by removing the fiber optic bundle 64 to provide a hollow wave guide through the flexible shaft 7 for conveying microwave energy from a suitable magnatron at the source 66 to the radiant energy distribution head 8 where it is directed through the balloon 20 onto the walls of the body cavity surrounding the head 8. The microwave energy is preferably adjusted to heat the inner surface of the body cavity so as to preferentially kill bacteria and other microorganisms living at the surface or lining of the body cavity.

Radio wave energy can be provided using the apparatus of FIGS. 3 and 4, but without a vacuum in the tube 28 between the electrodes 16 and 18. Instead, a radio frequency field can be set up between the electrodes 16 and 18 to produce heating of the body tissue when the body tissue is placed adjacent to or between the electrodes. To provide the radio frequency field, a powerful RF oscillator can be applied across the electrodes 16 and 18 so as to heat the body tissue between them, as the body tissue acts as a dielectric of a capacitor in which dielectric losses cause heating within the tissue. The RF oscillator can, if desired, be followed by RF amplifier stages for generating high frequency currents that produce heat within the part of the body cavity that is being treated for destroying the pathogenic bacteria on or within the tissue. Other forms of radio wave energy known to those skilled in the art can also be used for destroying microorganisms. In this embodiment of the invention, the balloon 20 can be eliminated since it is generally desirable to position the tissue being treated against or between the electrodes 16 and 18.

All publications and patents are herein incorporated by reference to the same extent as if each individual publication or patent was specifically and individually indicated to be incorporated by reference.

Other forms of the invention will now be described in connection with FIGS. 9–17. Refer now especially to FIGS. 9–12.

Figure 9:
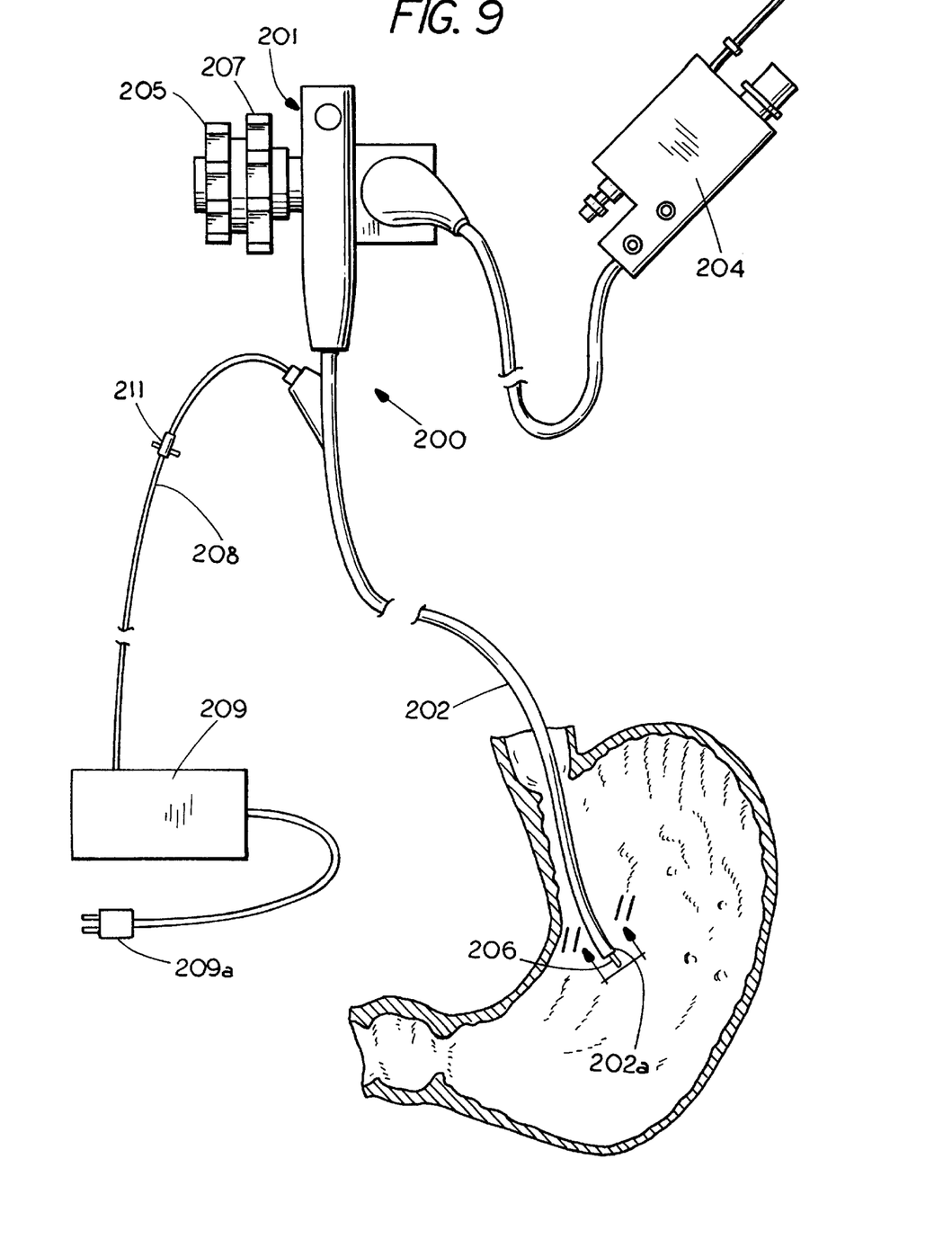
FIG. 9 is a vertical cross-sectional view showing the use in the stomach of another form of the invention.
Figure 11:
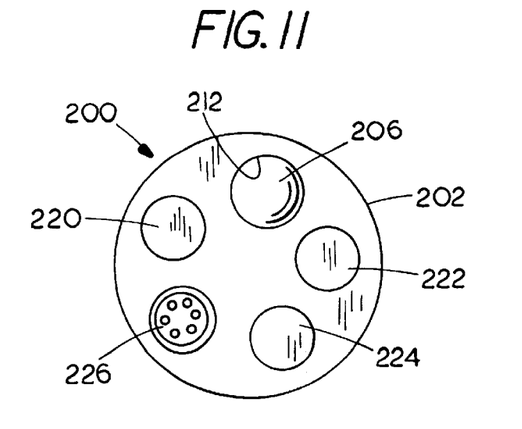
FIG. 11 is an end view taken on line 11—11 of FIG. 1 on a larger scale.
Figure 13:
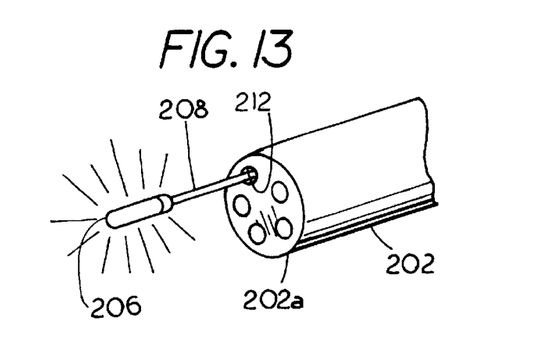
FIG. 13 is a perspective view similar to FIG. 12 with the lamp fully extended to a deployed position ready for use.

In FIG. 9 is shown a surgical instrument 200 which has a control head 201, a shaft 202 which in this case is flexible, a light source 204 for viewing, and a radiation source comprising a lamp 206 which is connected by means of a cord 208 to a suitable power supply 209. The instrument 200, including the shaft 202, control head 201 and viewing lamp 204, can be any suitable conventional and commercially available endoscope, preferably of the type having control knobs 205 and 207 for controlling the angular positioning of the instrument head or tip 202a. The shaft 202 of the instrument 200 has a longitudinally extending passage indicated at 212, the distal open end of which is shown in FIG. 11. Electrically insulated conductors 208a and 208b (FIGS. 14–16) are held in the cord 208 which is itself slidably supported in the passage 212 so that the lamp 206 can be withdrawn into the shaft 202 or extended to a deployed position by means of a handle 211 (FIG. 9) as shown in FIG. 13 when it is to be used. The electrical conductors 208a and 208b are connected at their proximal ends to the power supply 209. The power supply 209 can be of any suitable known, commercially available construction including an energy storage capacitor and a triggering circuit, preferably a computer-controlled triggering circuit.

Figure 10:
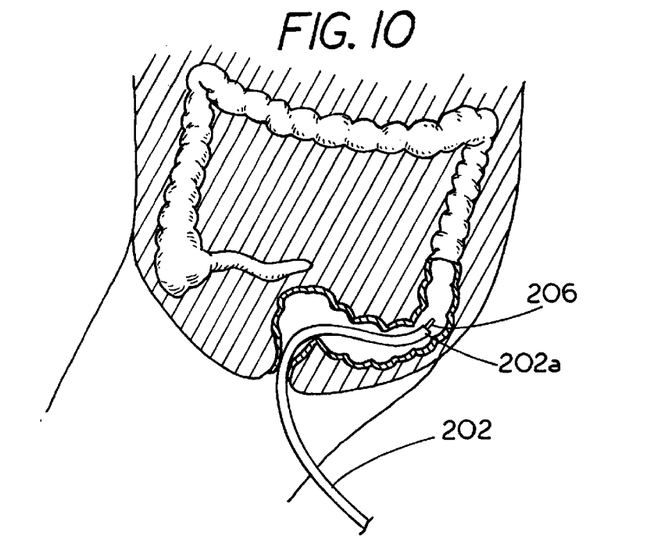
FIG. 10 is a vertical cross-sectional view showing the use of the invention of FIG. 9 in the colon.

While the lamp 206 can comprise any suitable lamp for producing radiation to kill or debilitate pathogenic bacteria, a preferred lamp 206 comprises either an ultraviolet lamp, such as a mercury vapor lamp, or a flash lamp formed from fused quartz, e.g. a xenon arc flash lamp, that can be made to pulse or flash periodically at selected timed intervals. One preferred lamp comprises a filtered short-arc xenon lamp as a radiation source for producing ultraviolet radiation. While radiation at various wavelengths can be used, one preferred range is ultraviolet light of about 200–400 nm. Good results have been obtained in debilitating pathogenic bacteria with a xenon flash lamp producing UV light between about 250–270 nm, with 258 nm being optimal for typical pathogenic bacteria. The flash lamp 206 is operated by a triggered discharge of energy from the electrolytic storage capacitor contained in the power supply 209 to produce a very short burst of high intensity light. The power supply 209 is provided with AC power from a wall plug 209a. A computerized control also contained in the power supply 209 actuates a triggering circuit which causes the xenon gas to suddenly become a low resistance path, at which time the energy stored in the electrolytic capacitor discharges through the flash lamp or tube 206, resulting in a short duration, brilliant, burst of light radiation that contains ultraviolet light. The computer causes the lamp 206 to flash at selected timed intervals, e.g., every five seconds, but the interval can be changed as desired by reprogramming the computer. The radiation from lamp 206 spreads out through a complete circle of 360° in all directions, to thereby debilitate or kill the pathogenic microorganisms, e.g. *H. pylori* that are present in the stomach. The invention is shown during use in the stomach in FIG. 9 for killing or debilitating *H. pylori*. In FIG. 10 the invention is shown in the colon for killing or debilitating pathogenic organisms that are present in cases of inflammatory bowel diseases such as ulcerative colitis, Crohn's disease or cytomegalovirus ulcers.

Billions of many different types of bacteria proliferate normally in the bowel. The body, however, sometimes cross-reacts to either pathogenic or normal bacteria. Occasionally, after sensing the presence of normal bowel flora, the body attacks one or more of the bowel flora species as a pathogen, setting up a chronic inflammatory state which makes the patient feel sick. Other gastrointestinal infections are caused by *H. pylori* as described above. To cure these conditions, in accordance with the present invention as shown in FIGS. 9–17, microorganisms in the colon or other parts of the digestive tract are either killed or debilitated by ultraviolet light, either from a mercury vapor lamp or from a pulsed xenon flash lamp as described. In one preferred protocol in accordance with the invention, following sterilization of the colon or other part of the bowel, the digestive tract is repopulated with probiotic bacteria, i.e., innocuous bacteria to which the body does not react adversely. In the preferred regimen, the probiotic bacteria are administered indefinitely with meals to reestablish a harmless flora that approximates the flora found in the gut under normal conditions.

Prior to using the instrument 200, in order to assure that the pathogenic bacteria are eliminated, in vitro kill studies are conducted. The kill studies are then used to determine how much radiation is required to achieve desired bacterial counts. Then, when the lamp 206 is used later in the stomach or intestine, the correct amount of radiation at the particular wavelength will be known for the lamp 206 that is being used. Thus, the microbicidal effectiveness of a given lamp is determined by the kill studies conducted in vitro for the lamp that is used later in treating human patients. As already mentioned, very good results were obtained with ultraviolet light of from about 250–270 nm, with 258 nm being optimum. To repopulate the bowel, any suitable commercially available probiotic bacteria can be employed. One preferred probiotic bacteria formulation is shown below in Table 1.

TABLE 1

| Probiotic Bacteria | Quantity |
| --- | --- |
| *Lactobacillus acidophilus* | 5 billion/gram |
| *Lactobacillus plantarum* | 5 billion/gram |
| *Lactobacillus rhamnosus* | 5 billion/gram |
| *Bifidobacterium infantis* | 5 billion/gram |
| *Bifidobacterium lactis* | 5 billion/gram |

TABLE 1-continued

| Probiotic Bacteria | Quantity |
| --- | --- |
| *Bifidobacterium longum* | 5 billion/gram |
| *Streptococcos Thermophilus* | 5 billion/gram |

The probiotic is administered either as tablets or capsules, typically taken three times a day indefinitely or until the natural background flora of the digestive tract is reestablished.

Figure 12:
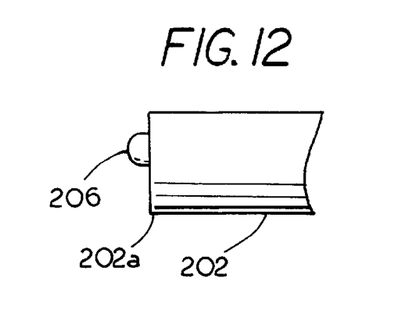
FIG. 12 is a side elevational view showing the distal end of the shaft of the instrument with a lamp as a radiation source, partially extended from the end of the instrument shaft.

Refer now to FIG. 11 which illustrates in more detail the construction of the lower end of the shaft 202 of the endoscope 200. Illumination is provided conventionally by the light source 204 through fiber optics to illumination ports 220 and 222 to enable the surgeon to see clearly through a viewing port 224 where radiation is to be applied. The endoscope 200 can also be provided with a spray nozzle 226 for washing debris away from the area around the end of the shaft 202 or for cleaning the lamp 206. To protect the lamp 206 while the shaft 202 of instrument 200 is being inserted into a body cavity, the lamp 206 is withdrawn into the shaft 202 as shown in FIG. 12 by means of a handle 211 (FIG. 9) so that the lamp 206 is either completely or almost completely recessed inside the lower end 202a of the shaft 202. However, when the lamp 206 is to be used, it is extended as far as desired by the surgeon to a deployed position as shown in FIG. 13, allowing the ultraviolet radiation to be transmitted in all directions.

Figure 14:
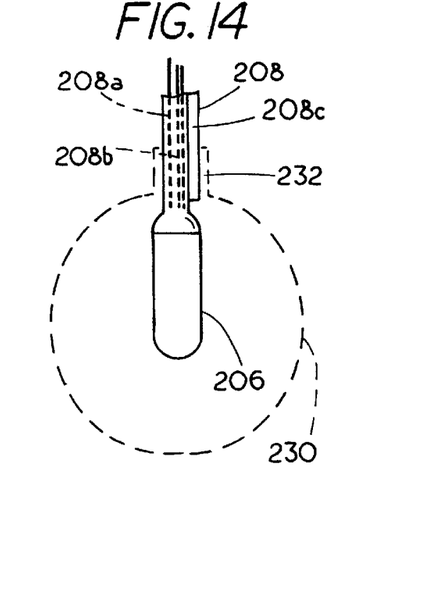
FIG. 14 is a side elevational view partly in section showing the lamp enclosed in an optional inflated balloon.

Refer now to FIG. 14. FIG. 14 illustrates an optional inflatable balloon 230 surrounding the lamp 206 and secured, e.g., by means of a suitable medical adhesive at 232, to the end of cord 208 which contains electrical conductors 208a and 208b and an air passage 208c for inflating the balloon 230 after the lamp 206 has been inserted into the stomach or bowel for positioning and stabilizing the lamp 206 in the body cavity as described hereinabove.

Figure 15:
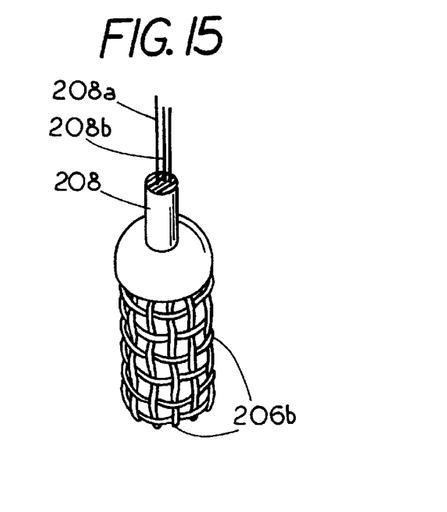
FIG. 15 is a perspective view of a lamp enclosed in a protective screen.
Figure 16:
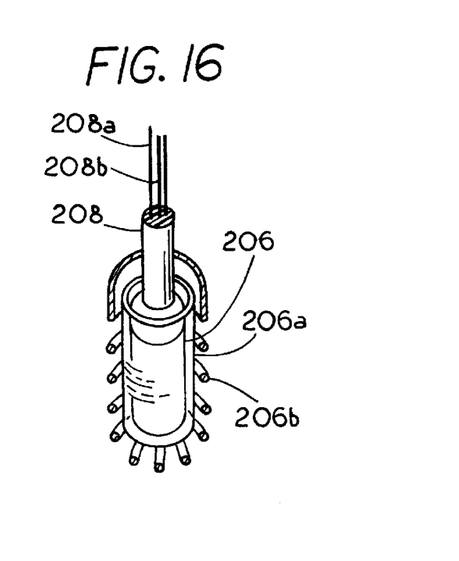
FIG. 16 is a perspective view similar to FIG. 15 but partly broken away to show the inner structure.

Refer now to FIGS. 15 and 16 which illustrate the lamp 206 in more detail These figures show how the lamp 206 is contained within a tubular quartz enclosure 206a which serves as a shield for filtering out heat radiation but, if desired, can also be used to restrict the wavelength of the light transmitted to the lining of the body cavity to a desired range.

During use, the lamp 206 could in some cases become fairly warm over extended periods of use. To prevent the patient from being injured by contact with a heated or broken lamp, a protective screen 206b is placed around the quartz shield 206a. Screen 206b can be formed from any suitable material such as plastic, metal or other material including synthetic fibers, e.g., carbon or Kevlar®, embedded in a plastic matrix.

Figure 17:
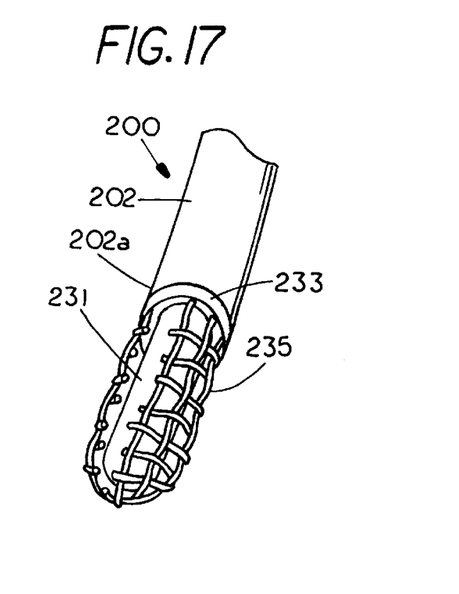
FIG. 17 is a perspective view showing the use of a lamp of a larger size as a radiation source.

Refer now to FIG. 17. In FIG. 17, a flash tube of a size larger than lamp 206 is provided. In this case the tube 231 is about the same diameter as the shaft 202. It is rigidly, i.e. directly, connected by means of a coupling at 233 to the tip 202a of the shaft 202 of the endoscopic instrument 200 and is positioned by manipulating the tip 202a through the use of cable controls 205 and 207. In this embodiment, the cord 208 is not slidably supported in shaft 202. The lamp 230 is surrounded by a protective screen 235 to prevent it from coming in contact with the lining of the stomach or bowel in case it becomes heated during use or breaks.

The invention will be better understood by reference to the following examples.

Following symptoms, including stomach discomfort, "heart burn," and/or pain, a tentative diagnosis by the physician of stomach ulcers is made which is later confirmed by an endoscopic examination. The diagnosis can then be further confirmed with standard enzymatic tests to detect the presence of *H. pylori*. Treatment using the present invention is then begun. Following standard sedation, the shaft 202 of the endoscope 200 is inserted through the esophagus (FIG. 9). The head or tip end 202a of the shaft 202 is then positioned as required under the supervision of the physician and the power supply 209 is turned on, thereby activating the computer contained in the power supply 209 causing the capacitor to discharge periodically through the mercury vapor or xenon arc lamp 206, e.g., once every five seconds until treatment is concluded. The lamp 206 is repositioned as necessary to provide adequate treatment to all of the affected areas, until the bacteria are either killed or incapacitated. The instrument 200 is then withdrawn.

Following a diagnosis of inflammatory bowel disease, such as ulcerative colitis or Crohn's disease, the bowel is cleansed conventionally. The patient is sedated in the usual manner, and the shaft 202 of the endoscope 200 is then inserted through the rectum and advanced to the infected area to be treated (FIG. 10). The distal end 202a of the instrument 200 is then positioned where treatment is required and the lamp 206 is extended from a recessed position as shown in FIG. 12 to the extended position of FIG. 13 in proximity to the lesions on the lining of the colon that require treatment. The lamp 206 is then actuated to produce a series of flashes that provide optimum exposure to the ultraviolet radiation until the pathogenic bacteria are killed or debilitated. The patient is then placed on a regimen of probiotics as already described for an indefinite period so as to reestablish the growth of innocuous flora within the bowel.

In another possible variation of the invention, following a mechanical prep, an antibiotic prep is used. A light-sensitizing medication is administered to the patient so that the light is preferentially absorbed by the bacteria within the colon, rather than by human cells. Any suitable light-sensitizing medicine can be used, such as any of the suitable protoporphyrin compounds known to those skilled in the art for preferentially absorbing the ultraviolet radiation so as to provide a more effective bacteriocidal action.

Many variations of the present invention within the scope of the appended claims will be apparent to those skilled in the art once the principles described herein are understood.

What is claimed is:

1. An apparatus for killing or debilitating pathogenic microorganisms in the treatment of an infectious gastrointestinal ailment, within a body cavity of a patient including gastritis, gastric ulcer, duodenal ulcer, gastric cancer, gastric lymphoma, inflammatory bowel disease, cytomegalovirus ulcers, ulcerative colitis, or Crohn's disease, said apparatus comprising:

an instrument body having an elongated shaft for insertion into a body cavity of the patient, a light radiation source connected to the shaft for destroying or debilitating microorganisms within the body of the patient, said light radiation source comprising a lamp for exposing an interior wall of the gastrointestinal tract of the patient to light radiation, the lamp being constructed to produce radiation that immediately kills or debilitates the microorganisms through apoptosis or program cell death by preventing further replication thereof through mutation or disruption of metabolic processes, such that the light radiation transmitted from the lamp to the wall of the gastrointestinal tract surrounding the shaft of the apparatus kills or debilitates pathogenic microorganisms supported on or within the epithelium lining the body cavity that is being treated without damage, destruction or ablation of the wall of the body cavity to thereby reduce or alleviate the symptoms of said ailment.

2. The apparatus of claim 1 wherein the lamp is a mercury vapor lamp.

3. The apparatus of claim 1 wherein the lamp is a xenon gas lamp.

4. The apparatus of claim 1 wherein the lamp is affixed by being mounted upon the distal tip of the shaft.

5. The apparatus of claim 1 wherein the lamp is surrounded by an optical filter for modifying the wavelength of the light transmitted to the lining of the body cavity of the patient.

6. The apparatus of claim 1 wherein a protective screen surrounds the lamp to prevent the lamp from injuring the body tissue of the patient.

7. The apparatus of claim 1 wherein the lamp is constructed to produce ultraviolet light radiation at a wavelength between about 200 nm and 400 nm.

8. The apparatus of claim 1 wherein the shaft is a fiber optic bundle, the radiation source is a light source that is coupled to a proximal end of the fiber optic bundle and is located outside of the body of the patient for passing light energy through the fiber optic bundle into the body cavity of the patient to destroy the microorganisms.

9. The apparatus of claim 1 wherein the shaft has one or more cables for manipulating a distribution head at the distal end of said shaft to point the head toward different areas of the body cavity that require treatment.

10. The apparatus of claim 1 wherein the shaft has a viewing port extending therethrough to enable an operator to see where radiation is to be applied.

11. The apparatus of claim 1 wherein the light radiation source is a lamp that is mounted at a distal end of the shaft which during use is located within the body of the patient for directing light radiation from the distal end of the shaft onto the interior wall of the gastrointestinal tract.

12. The apparatus of claim 1 wherein the lamp is a laser.

13. The apparatus of claim 11 wherein the lamp is a laser.

14. An apparatus for killing or debilitating pathogenic microorganisms in the treatment of an infectious gastrointestinal ailment, within a body cavity of a patient including gastritis, gastric ulcer, duodenal ulcer, gastric cancer, gastric lymphoma, inflammatory bowel disease, cytomegalovirus ulcers, ulcerative colitis, or Crohn's disease, said apparatus comprising:

an instrument body having an elongated shaft for insertion into a body cavity of the patient, a light radiation source connected to the shaft for destroying or debilitating microorganisms within the body of the patient, said light radiation source comprising a pulsed xenon arc lamp for exposing an interior wall of the gastrointestinal tract of the patient to light radiation, such that the light radiation transmitted from the lamp to the wall of the gastrointestinal tract surrounding the shaft of the apparatus kills or debilitates pathogenic microorganisms supported on or within the epithelium lining the body cavity that is being treated without damage, destruction or ablation of the wall of the body cavity to thereby reduce or alleviate the symptoms of said ailment.

15. An apparatus for killing or debilitating pathogenic microorganisms in the treatment of an infectious gastrointestinal ailment, within a body cavity of a patient including gastritis, gastric ulcer, duodenal ulcer, gastric cancer, gastric lymphoma, inflammatory bowel disease, cytomegalovirus ulcers, ulcerative colitis, or Crohn's disease, said apparatus comprising:

an instrument body having an elongated shaft for insertion into a body cavity of the patient, a light radiation source connected to the shaft for destroying or debilitating microorganisms within the body of the patient, said light radiation source comprising a lamp that is moveable with respect to the shaft between a recessed position inside the shaft and an extended position spaced from a distal tip of the shaft for exposing an interior wall of the gastrointestinal tract of the patient to light radiation, such that the light radiation transmitted from the lamp to the wall of the gastrointestinal tract surrounding the shaft of the apparatus kills or debilitates pathogenic microorganisms supported on or within the epithelium lining the body cavity that is being treated without damage, destruction or ablation of the wall of the body cavity to thereby reduce or alleviate the symptoms of said ailment.

16. An apparatus for killing or debilitating pathogenic microorganisms in the treatment of an infectious gastrointestinal ailment within a body cavity of a patient including gastritis, gastric ulcer, duodenal ulcer, gastric cancer, gastric lymphoma, inflammatory bowel disease, cytomegalovirus ulcers, ulcerative colitis, or Crohn's disease, said apparatus comprising:

an instrument body having an elongated shaft for insertion into a body cavity of the patient, a light radiation source connected to the shaft for destroying or debilitating microorganisms within the body of the patient, said light radiation source comprising a lamp for exposing an interior wall of the gastrointestinal tract of the patient to light radiation, a power supply having a control wired to the lamp for providing the lamp with timed pulses of electrical current for causing the lamp to flash at timed intervals with bursts of light radiation, such that the light radiation transmitted from the lamp to the wall of the gastrointestinal tract surrounding the shaft of the apparatus kills or debilitates pathogenic microorganisms supported on or within the epithelium lining the body cavity that is being treated without damage, destruction or ablation of the wall of the body cavity.

17. A method of use of a surgical apparatus having a body with a shaft terminating in a distal tip, and a means for directing light radiation from the apparatus onto the lining of a body cavity for treating a gastrointestinal ailment of a patient including at least one of the following: gastritis, gastric ulcer, duodenal ulcer, gastric cancer, gastric lymphoma, inflammatory bowel disease, cytomegalovirus ulcers, culcerative colitis or Crohn's disease, said method comprising:

inserting the shaft of the surgical apparatus into the body of the patient so as to place the distal tip of the apparatus within the gastrointestinal tract of the patient, irradiating the body cavity of the patient with light radiation so as to kill or debilitate microorganisms lining the body cavity without damage destruction or ablation of the body cavity of the patient, said inserting and irradiating steps improving or alleviating one or more of the symptoms of said gastrointestinal ailment.

18. The method of claim 17 including the step of irradiating the gastrointestinal tract of the patient with ultraviolet light having a wavelength of between about 200 nm and 400 nm.

19. The method of claim 17 including the step of irradiating the lining of the body cavity with ultraviolet light having a wavelength of between about 250 nm and 270 nm.

20. The method of claim 17 wherein the light radiation is provided by a mercury vapor lamp and including the step of transmitting ultraviolet light from the mercury vapor lamp to the wall of the body cavity of the patient.

21. The method of claim 17 wherein the light radiation is provided by a xenon arc lamp and including the step of providing a series of times pulses of electrical current to the xenon arc lamp to cause the lamp to flash for providing bursts of ultraviolet light at times intervals.

22. The method of claim 17 wherein, following light irradiation, the patient is treated by administering a probiotic to the patient for establishing the growth of innocuous intestinal flora within the intestine of the patient.

23. The method of claim 22 wherein the flora comprises a mixture of non-pathogenic probiotic bacteria and including administering the non-pathogenic probiotic bacteria to the patient until the growth of flora is reestablished within the intestine of the patient.

24. The method of claim 17 wherein the tip of the instrument is inserted into the digestive tract for exposing the lining of the digestive tract to ultraviolet light and, following treatment by exposure to light radiation, the patient is further treated by administering to the patient a probiotic mixture of bacteria that includes one or more of the following: *Lactobacillus acidophilus, Lactobacillus plantarum, Lactobacillus rhamnosus, Bifidobacterium infantis, Bifidobacterium lactis, Bifidobacterium longum* and Streptococcos Thermophilus.

25. The method of claim 17 wherein the lining of the body cavity is irradiated with ultraviolet radiation having a wavelength between about 200 nm and 400 nm.

26. The method of claim 17 including the step of administering to the patient a light-sensitizing medication that is preferentially absorbed by pathogenic bacteria within the colon for enhancing the absorption of the ultraviolet light thereby.

* * * * *